United States Patent [19]

Hüschelrath et al.

[11] 4,452,086
[45] Jun. 5, 1984

[54] ELECTRODYNAMIC ULTRASONIC TRANSFORMER

[75] Inventors: Gerhard Hüschelrath, Laufach; Karl Laudenbach, Giessen, both of Fed. Rep. of Germany

[73] Assignee: Nukem GmbH, Hanau, Fed. Rep. of Germany

[21] Appl. No.: 312,977

[22] Filed: Oct. 20, 1981

[30] Foreign Application Priority Data

Nov. 12, 1980 [DE] Fed. Rep. of Germany ....... 3042645

[51] Int. Cl.³ ............................................. G01N 29/00
[52] U.S. Cl. .................................... 73/643; 174/126 R
[58] Field of Search .................. 73/643; 335/282, 299; 336/222; 174/126 R; 420/442, 459, 487

[56] References Cited

U.S. PATENT DOCUMENTS

| 811,859 | 2/1906 | Marsh | 420/442 |
| 4,102,207 | 7/1978 | Frost | 73/643 |

FOREIGN PATENT DOCUMENTS 426716  1/1975  U.S.S.R. ............................... 73/643

OTHER PUBLICATIONS

F.M. Sebast et al., "Electrical Resistances and Temperature Coef. of Nickel-Copper Chromium and Nickel-Copper Manganese Alloys", *Transactions of AES*, vol. 29, pp. 569-578, Apr. 1916.

H. D. Holler, "Observations on Failure of 80 Nickel 20 Chromium Alloy at Excessive Temperatures", The Electrochemical Society, Preprint 92-7, pp. 101-107, Oct. 1947.

K. O. Legg et al., "Flaw Detection in Metals Using Electromagnetic Sound Generation", *J. Phys. D. Appl. Phys. (GB)*, vol. 3, No. 10, pp. 61-63, Oct. 1970.

Journal "Rev. Sci, Instrument", vol. 46, No. 7, Jul. 1975, pp. 931-932.

*Primary Examiner*—Stephen A. Kreitman
*Attorney, Agent, or Firm*—Cushman, Darby & Cushman

[57] ABSTRACT

An electrodynamic ultrasonic transformer, having at least one exciting coil and one receiving coil, for use in ultrasonic nondestructive material testing in order to reduce the dead times and to remove or, respectively, minimize negative influences occurring during the measuring of different test piece material and at distance variations without adversely affecting the signal/noise ratio. Those parts of the exciting coil and/or receiving coil designed for current conducting are preferably made of resistance material which is suitable for structural elements embodying electric resistors, and which material will not essentially obstruct the current flow during the exciting phase of the current, and after termination of the excitation will rapidly reduce the energy stored in stray and coupling fields.

11 Claims, 1 Drawing Figure

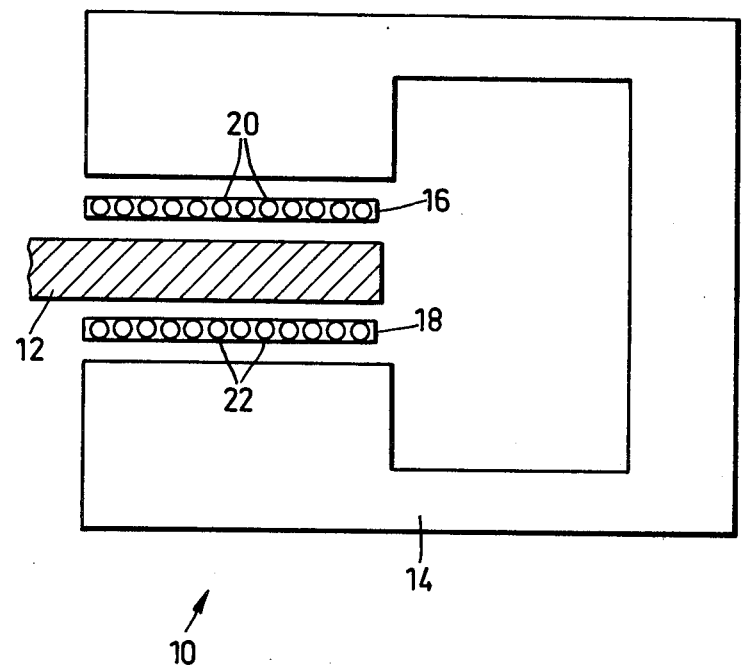

ELECTRODYNAMIC ULTRASONIC TRANSFORMER

The invention is directed to an electrodynamic ultrasonic transformer having at least one exciting coil and one receiving coil, for the nondestructive testing of material by means of ultrasonics.

In order to maintain high quality standards and optimum production in the manufacture of sheet-metal and especially of steel tubes, there is a trend toward large scale use of ultrasonic measuring systems, among them also wall thickness measuring systems, based on the electrodynamic excitation of ultrasound. The electrodynamic excitation of ultrasound is based on the fact that a force is exercised on a current-carrying body in a magnetic field, which force is acting vertically on a plane defined by the magnetic field vector and the current vector. Via a pole shoe configuration, an electromagnet generates the required magnetic field. Within the range of this magnetic field, via a current pulse in a transformer coil, an eddy current pulse is excited in the test piece. Of course, the strength of the power pulse generated in such a manner and thus the strength of the ultrasonic pulse is contingent on the eddy current force, however, above all on the magnetic field force. To generate ultrasonic pulses of sufficient strength in the test piece, field strengths of 1 to 1.5 Tesla and eddy current strengths of some amperes on the surface of the test piece are necessary, which can only be obtained if the electrodynamic transformer head is arranged very close to the test piece.

The accuracy of wall thickness measuring is primarily dependent on the properties of the generated field of sound, which after the above mentioned method are essentially determined by the direction of the magnetic field and the wiring direction of the exciting coil of the electrodynamic transformer.

In the 3rd technical-scientific report to RS 102-18, Part II "Electrodynamic Systems," of the Fraunhofer-Gesellschaft zur Foerderung der angewandten Forschung e.V. (association for promoting the practical research), Messrs. W. Mohr and W. Repplinger have described an electrodynamic ultrasonic transformer, of which the exciting coils and the receiving coils are made of varnished copper wire, a material with good electricity conducting power. In order to generate sound waves of sufficient strength, this ultrasonic transformer requires high currents on the part of the exciting winding. Since the receiving circuits present a high sensivity, even little oscillation voltages of the exciting coil are also transmitted to the receiving coil and amplified in the receiver. The echo signals from the test piece are within the range of some millivolts. Therefore, at an undamped excitation a considerable dead time of several microseconds will occur till the oscillations of the exciting coil have subsided. During this time it is not possible to receive reflected signals and to process them. This means that e.g. with steel tubes of larger dimensions no wall thicknesses up to approx. 10 mm can be tested due to the dead time. Thus an inspection by means of electrodynamic transformer below a certain thickness of the material is not possible at all in the conventional manner or only via multiple reflected echoes.

For reducing the dead time, it is known in the above mentioned document to damp the receiving circuit during the transmission signal and the subsequent final oscillation, as well as the transmitting circuit during the final oscillation only. For damping, a frequency thyristor is connected to the transformer coil, which thyristor will short-circuit the coil during the damping periods. However, an effective reduction of the dead time and thus of the zone in the material that cannot be inspected, can only be achieved by means of thyristors for high performance and with rather short operating times. However, if thyristors have to switch high currents, this will result in limits to the switching times.

The presently known electrodynamic ultrasonic transformers have the following characteristics concerning the damping: the damping of the exciting and receiving oscillatory circuits is governed by the eddy currents induced in the test piece. Each change to the measuring arrangement influencing the generation of the eddy currents in the test piece thus directly affects the damping of the oscillatory circuit.

This can happen by changing the distance of the transformer to the test piece or even by changing material of the test piece or, respectively, their structural differences and surface condition. The effect of a damping of the oscillatory circuit is indicated by an extended dead time, a changed form of the echo pulse (width, height) as well as a changed ratio of signal to noise.

Although one can compensate for the influence of differences in material at least to some extent by adapting the outer switching of the coils when changing material, this cannot be done when distance variations between the ultrasonic transformer and the test piece occur in practical operation. This is expressed by the relatively narrow distance tolerances applying to conventional constructions (e.g. 0.5 to 0.7 mm distance from the test piece according to the above explained arrangement).

It is the object of the invention to improve an electrodynamic ultrasonic transformer of the initially described kind in such a manner that the dead times will be reduced and the negative influences removed or, respectively, minimized as much as possible, which occur at the measurement of different test piece material and changes of the distance, without essentially impairing the signal/noise ratio.

According to the invention, this problem is solved in that those components of the exciting and/or receiving coils serving as current conductors, are made of resistance material being suitable for structural elements configuring electric resistors, and which during the exciting phase of the current does not essentially obstruct the current flow, and after completed excitation quickly reduces the energy stored in stray and coupling fields.

By such an arrangement the dead time of the measuring instrument, and thus the dimension of the uncontrollable zone of the test piece, is considerably reduced. An essential advantage over known electrodynamic ultrasonic transformers is that it offers a possibility to detect defects in test pieces of small wall thickness. In addition thereto, the accuracy of the measurement is increased by the inclusion of wall zones that could not be grasped. While with the known electrodynamic ultrasonic transformers even little changes of distance between the transformer and the surface of the test piece will influence the measuring results to an undesirably large extent, this influence is considerably less with the above described instrument. As it is not necessary anymore to keep very accurate distances, this instrument can be handled much simpler and quicker.

In a preferred embodiment, the specific resistance of the resistance material at 20° C. is about ten to fifty times higher than the specific resistance of conducting copper wire at 20° C. The conditions as to reduced dead time, the utilization of the influences of changed distances between the ultrasonic transformer and the surface of the test piece and a high signal/noise ratio are very favorable in this range.

Preferably the exciting coil and the receiving coil respectively are made of different resistance material. Hereby it is expedient to choose for the exciting winding a smaller resistance coating than that for the receiving winding. Thereby one can achieve a high performance of the ultrasonic transformer at short dead times.

In a preferred embodiment the resistance material is composed of alloys with high percentages of nickel and chromium. Such alloys are also employed as heating conductor material. Among these alloys are CuNi 30 Fe, CuNi 5 Fe, NiCr 8020, NiCr 6015 and NiCr 3020.

Preferably the receiving coil is made of NiCr 6015. This is a heating conductor alloy, which according to DIN 17470 is composed to 60% of Ni, to 15% of Cr and to 25% of Fe.

It is expedient to make the exciting coil of CuNi 11. Aside from forging aluminium alloys of the copper with a high nickel percentage, also resistance pastes and conducting adhesives available on the market are well suited for this purpose. These materials are preferably made of metal powder or metal alloy powder or, resp. carbon powder and a binding agent.

The idea to make the windings of the coils of resistance material has turned out to be a surprisingly simple optimum solution.

By an adequate resistance load of the respective coils, the self-oscillations of the coil system can be damped especially well.

Hence it follows that not only the switching of the oscillatory circuits is governing the dead time but also to an essential extent the natural frequencies of the coils. However, by an outer damping with resistors connected to the coils, these natural frequencies cannot be damped. This can only be achieved by a suitable resistance coating in the coil material. In the resistor of the coil material the energies existing in the stray and coupling fields are quickly reduced.

On principle, the reduction of the residual fields takes place so much quicker the higher the resistance coating is. However, for technical reasons it is not possible e.g. with the exciting winding, to force up the resistance coating to whatever height you choose, since the strongest possible current shall flow through the exciting winding. Consequently the resistance coating of the exciting coil must be chosen in such a manner that there will be an adaption to the internal resistance of the transmitter, but as a rule this resistance is rather little.

With the receiving winding the conditions are fundamentally different. Here currents of little intensity shall be detected. As a rule, the input connections of the receiving amplifiers are of high ohmic resistance, so that the receiving winding, too, can be of high ohmic resistance. Therefore a high resistance coating can be tolerated here.

In consideration of the above indicated demands on connection techniques, as well as a good mechanic tensile strength at a low price and an easy procurement, it has proved to be especially favorable to use coil material composed of alloys with percentages of nickel and chromium, where the NiCr 6015 for its high resistance coating and good working properties is especially suited for receiving windings and the CuNi 11 especially for exciting windings, as coils made of CuNi 11 can be adapted exceptionally well to existing transmitters and can stand a high power load.

The exciting and receiving windings of the electrodynamic transformer, which are sensitive, must be must be safely mounted on a supporting plate. This also allows the processing of other resistance stock by different techniques than the winding of resistance wires. Thereby it is especially advantageous to apply a resistance paste directly on the material of the supports. Also a sputtering of the resistance material onto the supporting plates has proved to be especially favorable due to the evenly distributed material. By subsequent etching, scratching, slotting or any other known methods, applied to the distributed pastes or sputtered-on layers, the coil geometry as required in each case is produced.

Further characteristics as well as advantages of the invention will appear from the following detailed description of a preferred embodiment represented in the sole FIGURE of this patent.

The FIGURE is a diagrammatic view of an electrodynamic ultrasonic transformer 10, partially in cross-sectional view. The transformer 10 serves to test a steel band 12. A magnet yoke 14 generates a strong magnetic field, of which the field lines are in a direction essentially perpendicular to the surfaces of the steel band 12. Parallel to one surface of the steel band 12, an exciting coil 16 is arranged within the range of the magnetic field generated by the magnet yoke 14. On the other side of the steel band 12, parallel to the surface and within the range of the magnetic field, a receiving coil 18 is arranged. The exciting and the receiving coils 16, 18 each have windings of wires 20, 22 made of resistance material. The exciting coil 16 is connected to a high-frequency generator (not shown), producing high-power pulses. The receiving coil 18 is connected to a measuring receiver via amplifying and controlling connections (not shown). The wires 20 can be made of CuNi 11, while the wires 22 are composed of NiCr 6015.

The following examples shall show that the using of resistance material for the exciting and receiving windings exercises a surprisingly good solution to the problems discussed earlier. For three different substances there are indicated each time the coil impedances, the dead time as well as the signal to the noise ratio of the 3rd reflection of the beat from the back surface of transformer coils, once made of copper and once made of resistance material, where the coil parameters are chosen in such a manner that the coils had been adapted to the electronic connections (i.e. that the transmitting coils with the impedances should be at approx. 20Ω and the receiving coils at approx. 1.2 KΩ).

EXAMPLE 1

Coil Data (a)

Exciting winding
14 windings CuNi 11
coil diameter 14 mm
resistance coating 14,2 Ohm/m
cross-section of winding 0,12 mm (b)

Receiving winding
45 windings NiCr 6015
coil diameter 10 mm
wire cross-section 0,05 mm
resistance coating 592 Ohm/m The comparison coils with corresponding Cu wires had the same mechanical dimensions.
  Measuring frequency: 2 MHz.
  Material: St 37, 30 mm thick.
  The following characteristic data were established:

| For coils with the above indicated resistance material: | | |
|---|---|---|
| Impedance: | Z receiver | $= 1,24$ k$\Omega e^{-j44°}$ |
| Impedance: | Z transmitter | $= 23,6\Omega e^{j70°}$ |
| dead time: | t | $= 3,0$ $\mu$sec |
| signal/noise ratio: | S/N | $= 13$dB; |
| For coils with conducting copper wire (Cu = copper) | | |
| Impedance: | $Z_{ECu}$ | $= 1,1$ K$\Omega e^{j56°}$ |
| Impedance: | $Z_{SCu}$ | $= 20,5\Omega e^{j34°}$ |
| dead time: | $t_{cu}$ | $= 7,0$ $\mu$sec |
| signal/noise ratio: | S/N | $= 15$ dB |
| The respective data without test piece (= distance variation) | | |
| For coils with resistance material | | |
| Impedance: | Z receiver | $= 1,65$ k$\Omega e^{-j39°}$ |
| Impedance: | Z transmitter | $= 36$ $\Omega e^{j70°}$ |
| dead time: | t | $= 3,5$ $\mu$sec |
| For coils with copper | | |
| ECu $= 3,6$ k$\Omega e^{j87°}$ | | |
| SCu $= 40\Omega e^{j34°}$ | | |
| dead time not exactly measurable ($\approx 30$ $\mu$sec) | | |
| signal/noise ratio without echoes not measurable. | | |

EXAMPLE 2

With the same coil data and same measuring construction only the test piece has been exchanged:

| Material: P 41 MnV 5/2, thickness 24 mm | |
|---|---|
| Coils of resistance material | |
| Impedance | $Z_E = 1.25$ K$\Omega e^{-j44°}$ |
|  | $Z_S = 23.5\Omega e^{j24°}$ |
|  | $t = 2,8$ $\mu$sec |
| Signal/noise ratio: | S/N $= 9,9$ dB |
| Coils of copper | |
| Impedance | $Z_{ECU} = 1.2$ k$\Omega e^{j37°}$ |
|  | $Z_{Scu} = 20\Omega e^{j38°}$ |
| Dead time | $t_{Cu} = 7$ $\mu$sec |
| Signal/noise ratio: | S/N$_{cu} = 11$ dB |
| Example 3: as 1 and 2, however | |
| Material: | 535/A3, thickness 16 mm |
| Coils of resistance material | |
| Impedance | $Z_E = 1,23$ K$\Omega e^{-j44°}$ |
|  | $Z_S = 23,6\Omega e^{j23°}$ |
| Dead time: | $t = 2.8$ $\mu$sec |
| Signal/noise ratio | S/N $= 17,7$ dB |
| Coils of copper | |
| Impedance | $Z_{ECu} = 1,5$ K$\Omega e^{j30°}$ |
|  | $Z_{SCu} = 24,1\Omega e^{j70°}$ |
| Dead time: | $t_{cu} = 7$ $\mu$sec |
| Signal/noise ratio: | S/N$_{cu} = 19$ dB |

The examples clearly show the dead time reduced in round for the factor 2, as well as the obviously lessened dependency of the characteristic coil impedances on the material of the test piece and on the effect of distance variation, of the coils made of resistance material as compared to those being wound of copper wire.

With the exciting and receiving coils for electrodynamic transformers according to the invention it is therefore possible to reduce the dead time as well as to minimize the negative influences of different test piece material and distances without affecting adversely the signal/noise ratio.

We claim:

1. An electrodynamic ultrasonic transformer comprising:
  a magnet yoke having two poles for establishing a magnetic field between said poles into which a test piece can be placed;
  an exciting coil positioned between one of said poles and the test piece; and
  a receiving coil positioned between the test piece and other pole, the exciting and receiving coils having portions serving as current conductors fabricated from an electrical resistance-type material which during an exciting current flow does not substantially impede current flow in the exciting coil and which after excitation, rapidly dissipates energy stored in stray and coupling fields, the exciting and receiving coil portions being formed from different resistance materials, respectively.

2. A transformer according to claim 1 wherein the resistance-type materials used for the current conducting portions of the exciting and receiving coils have an electrical resistance at 20° C. that is in the range of 10-70 times that of the resistance of copper wire at 20° C.

3. An electrodynamic ultrasonic transformer for use in ultrasonic non-destructive material testing comprising:
  an exciting coil; and
  a receiving coil, parts of said coils serving as current conductors being made of resistance material, the specific resistance of the resistance material at 20° C. being in the range of 10-70 times that of the resistance of copper wire at 20° C.

4. An electrodynamic ultrasonic transformer according to claim 3, wherein the exciting coil and receiving coil are made of different resistance materials.

5. An electrodynamic ultrasonic transformer according to claim 3 or 4, wherein the receiving coil is made of NiCr 6015.

6. An electrodynamic ultrasonic transformer according to claim 3, wherein the exciting coil is made of CuNi 11.

7. An electrodynamic ultrasonic transformer according to claim 3, wherein the resistance material comprises a metal powder and a binding agent.

8. An electrodynamic ultrasonic transformer according to claim 3 wherein the resistance material comprises a metal alloy powder and a binding agent.

9. An electrodynamic ultrasonic transformer according to claim 3 wherein the resistance material comprises carbon and a binding agent.

10. An electrodynamic ultrasonic transformer according to claim 3, wherein the resistance material is applied to a carrier material.

11. An electrodynamic ultrasponic transformer according to claim 10 wherein the resistance material is applied to the carrier material by cathodic sputtering.

* * * * *